(12) United States Patent
Okano et al.

(10) Patent No.: US 6,660,863 B2
(45) Date of Patent: Dec. 9, 2003

(54) PROCESS FOR SYNTHESIZING ANHYDROECGONINE DERIVATIVE

(75) Inventors: Kyoko Okano, Sodegaura (JP); Osamu Itoh, Sodegaura (JP)

(73) Assignee: Nihon Medi-Physics Co., Ltd., Hyogo-ken (JP)

( * ) Notice: Subject to any disclaimer, the term of this patent is extended or adjusted under 35 U.S.C. 154(b) by 0 days.

(21) Appl. No.: 10/210,168

(22) Filed: Aug. 2, 2002

(65) Prior Publication Data

US 2003/0109708 A1 Jun. 12, 2003

Related U.S. Application Data

(62) Division of application No. 09/773,688, filed on Feb. 2, 2001.

(30) Foreign Application Priority Data

Feb. 2, 2000 (JP) ........................................ 2000-025145

(51) Int. Cl.[7] ............................................. C07D 451/02
(52) U.S. Cl. ..................................................... 546/124
(58) Field of Search ......................................... 546/124

(56) References Cited

U.S. PATENT DOCUMENTS 2,783,235 A  2/1957  Grundmann et al.

OTHER PUBLICATIONS

"Synthesis of 3–Arylecgonine Analogues as Inhibitors of Cocaine Binding and Dopamine Uptake", J. of Medicineal Chemistry, Kline, et. al., pp. 2024–2026.*
XP–001007747—John W. Bastable, et al.—"Solovolytic Rearrangements of Azabicyclic Compounds"; Received May 16, 1980—Published in 1981.
XP–002171260–Richard H. Kline, Jr. et al.—"Synthesis of 3–Arylecgonine analogues as Inhibitors of Cocaine Binding and Dopamine Uptake"; J. Med. Chem. 1990, 33, 2024–2027; Received Sep. 5, 1989.
XP–001007755—Von Dr. A. Heusner—"Experimentelle Ubergange zwischen Tropan–Derivaten und der Gruppe der Tropilidene, Tropone and Tropolone"; published Nov. 7, 1958.

* cited by examiner

*Primary Examiner*—Alan L. Rotman
*Assistant Examiner*—Binta Robinson
(74) *Attorney, Agent, or Firm*—Sughrue Mion, PLLC

(57) ABSTRACT

The present invention relates to a process for synthesizing an anhydroecgonine derivative without using cocaine as a starting material, and a process for synthesizing a phenyl-tropane derivative by using said anhydroecgonine derivative as an intermediate for the synthesis. The present invention provides a process for synthesizing an anhydroecgonine derivative which comprises reacting a cycloheptatriene derivative represented by the formula (1):

(1)

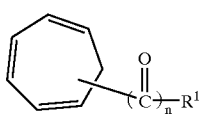

with a primary amine, a salt thereof or ammonia in the presence of a base to obtain an anhydroecgonine derivative, and a process for synthesizing a phenyltropane derivative by using said anhydroecgonine derivative. In the formula (1), n is an integer of 0 or 1; and $R^1$ is a cyano group in the case of n being 0, and $R^1$ is selected from an alkyl group and an aralkyl group in the case of n being 1.

3 Claims, No Drawings

PROCESS FOR SYNTHESIZING ANHYDROECGONINE DERIVATIVE

This is a divisional of application Ser. No. 09/773,688 filed Feb. 2, 2001; the disclosure of which is incorporated herein by reference.

BACKGROUND OF THE INVENTION

1. Field of the Invention

The present invention relates to a process for synthesizing an anhydroecgonine derivative that is an intermediate for synthesis of an alkaloid having the same tropane skeleton as that of cocaine having an affinity for dopamine transporters pharmacologically, and a process for synthesizing a phenyltropane derivative by using said anhydroecgonine derivative as an intermediate for the synthesis.

2. Related Art

Cocaine is an alkaloid contained in the leaves of, for example, coca (*Erythroxylon coca*) growing in the Andes in South America. A pure preparation of this alkaloid was isolated for the first time by Niemann et al. in 1860. Cocaine tastes bitter and its special effects such as numbness of tongue and sensory paralysis have been revealed. Freud and Koller applied cocaine to clinical use for the first time. In 1884, Freud extensively investigated the physiological effects of cocaine. On the other hand, Koller applied cocaine to a local anesthetic in the ophthalmic operation. Thereafter, local anesthesia using cocaine has rapidly come to be employed in various fields of medicine. Einhorn investigated the synthesis of a substitute for cocaine (Goodman, "Yakurisho", 8th ed., Hirokawa Shoten Ltd.). Since cocaine has recently been found to have an affinity for dopamine transporters, it has been shown that cocaine derivatives are useful as tracer ligands, in particular, radioactive tracers for imaging agents in nuclear medicine.

Cocaine blocks the uptake of dopamine into nerve cells because of its affinity for dopamine transporters that are membrane proteins capable of reuptake of dopamine released into synaptic clefts from dopamine nerve ending. In recent years, this mechanism of action of cocaine has been noticed in the field of nuclear medicine and attempts have been made to give a diagnosis by imaging of the dopamine transporters. Accordingly, radiolabeled products of various cocaine analogs were investigated. Neumeyer et al. found compounds such as 2β-carbomethoxy-3β-(4-iodophenyl)-tropane which are neuroprobes useful as radioactive tracers having an affinity for the dopamine transporters for use in single-photon emission computed tomography (SPECT) or positron emission tomography (PET) in nuclear medicine. It has been shown that the brain uptake and clearance from brain of these compounds are slower than those of cocaine itself, and that the uptake of the compounds into striatum substantially reflects the distribution of dopamine reuptake site (U.S. Pat. No. 5,310,912). In addition, Neumeyer et al. investigated various phenyltropane derivatives and consequently confirmed that N-(3-fluoropropyl)-2β-carbomethoxy-3β-(4-iodophenyl)nortropane is a compound further improved, for example, in pharmacokinetic problems such as residence time as compared with 2β-carbomethoxy-3β-(4-iodophenyl)tropane. It has been reported that the estimation of the change of dopamine nerve cells by imaging of striatum dopamine transporters with the radioiodinated (Iodine-123) phenyltropane derivatives gives useful information for early diagnosis of Parkinson's disease and judgment on the seriousness of this disease (Booiji et al., Eur. J. Nucl. Med., 1997, 24, 68–71).

At present, as shown in the scheme A exhibited hereinafter, the tropane skeleton as basic skeleton of cocaine is obtained as anhydroecgonine methyl ester by hydrolyzing cocaine as a starting material into ecgonine, dehydrating the ecgonine, and converting the dehydrated product to methyl ester (Kozikowski et al., J. Am. Chem. Soc., 1995, 38, 3086). From this anhydroecgonine methyl ester, there can easily be synthesized a derivative having an optically active tropane skeleton having the same absolute configuration as that of natural (−)-cocaine, such as 2β-carbomethoxy-3β-(4-iodophenyl)tropane or N-(3-fluoropropyl)-2β-carbomethoxy-3β-(4-iodophenyl)-nortropane. Cocaine, however, is designated as a narcotic because of problems such as drug dependence. For that reason, there are various difficulties in obtaining and handling cocaine. Therefore, there is desired the development of a process for synthesizing a compound analogous to cocaine which does not cause the difficulties.

Since early times, attempts have been made to synthesize a cocaine analogous (a tropane derivative) without using cocaine as a starting material. Robinson et al. synthesized tropinone by condensing a dialdehyde, methylamine and acetonedicarboxylic acid ethyl ester (Robinson et al., J. Chem. Soc., 1917, 762–768; Findlay et al., J. org. Chem., 1957, 22, 1385–1394). Neumeyer investigated the synthesis of 2β-carbomethoxy-3β-(4-iodophenyl)tropane using tropinone as a starting material (Neumeyer et al., J. Med. Chem., 1993, 36, 1914–1917). Tufariello et al. attempted stereoselective synthesis of cocaine (Tufariello et al., Tetrahedron Lett., 1978, 20, 1733–1736). However, in each of these synthetic processes, the synthesis should be carried out by producing cocaine or ecgonine methyl ester as an intermediate in the synthetic procedure. Carrying out the synthesis by replacing the substituent on the nitrogen atom with another substituent can be thought of but is disadvantageous in that it requires several additional steps. Grundmann et al. synthesized dl-ecgonidine and its ester from a cycloheptatrienecarboxylic acid derivative synthesized from benzene and a diazoacetic acid derivative, without producing an ecgonine derivative as an intermediate (Grundmann et al., Justus Liebigs Ann. Chem., 1957, 605, 24–32, and U.S. Pat. No. 2,783,235). However, no starting material other than the cycloheptatrienecarboxylic acid derivative is described in these references.

Reaction scheme A

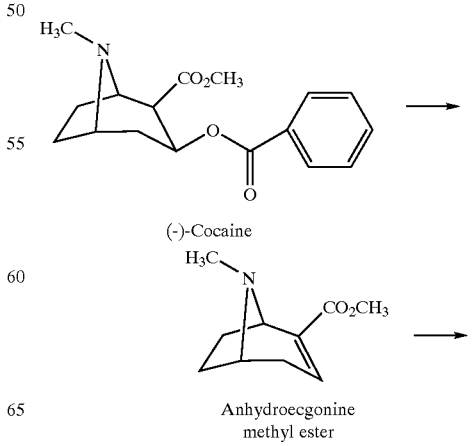

(−)-Cocaine

Anhydroecgonine methyl ester

-continued

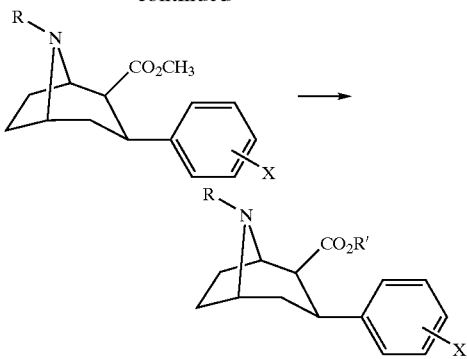

Since almost all of the above processes for synthesizing a tropane derivative are processes for synthesizing a racemic cocaine derivative, an optical resolution step is required for obtaining an optically active tropane derivative having the same absolute configuration as that of (−)-cocaine. For example, in order to obtain starting material for synthesizing various tropane derivatives, Grundmann et al. attempted the optical resolution of dl-ecgonidine ethyl ester by recrystallization and Wang et al. attempted the optical resolution of dl-carbomethoxytropinone by recrystallization. However, it is generally difficult to obtain a compound (1-form, (−)-form) having an extremely high optical purity, only by optical resolution by recrystallization. Selective synthesis of optically active anhydroecgonine methyl ester by an asymmetric synthetic method was also carried out by Davies et al. (J. Org. Chem., 1991, 56, 5696–5700, and Japanese Patent Application Kohyo No. 7-504665) and Node et al. (Tetrahedron Lett., 1999, 40, 5357–5360). However, neither of their synthetic processes can give a desired compound having a satisfactory optical purity, for example, because the processes comprise a large number of steps for the synthesis.

SUMMARY OF THE INVENTION

In view of such situation, the present invention is intended to provide a process for synthesizing an anhydroecgonine derivative useful as an intermediate for synthesis of a tropane derivative, without using cocaine as a starting material, and a process for synthesizing a tropane derivative by using said anhydroecgonine derivative as an intermediate for the synthesis.

One aspect of the present invention is directed to a process for synthesizing an anhydroecgonine derivative which comprises reacting a cycloheptatriene derivative of the formula (1) shown below with a primary amine, a salt thereof or ammonia.

That is, it is directed to a process for synthesizing an anhydroecgonine derivative which comprises reacting a cycloheptatriene derivative represented by the formula (1):

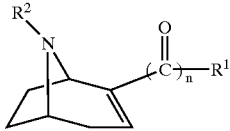

(1)

wherein n is an integer of 0 or 1; and $R^1$ is a cyano group in the case of n being 0, and $R^1$ is selected from an alkyl group and an aralkyl group in the case of n being 1, with a primary amine represented by the formula (2):

$$R^2NH_2 \quad (2)$$

wherein $R^2$ is a hydrogen atom, an unsubstituted alkyl group, a substituted alkyl group, an unsubstituted aralkyl group or a substituted aralkyl group, or a salt thereof or ammonia in the presence of a base to obtain an anhydroecgonine derivative represented by the formula (3):

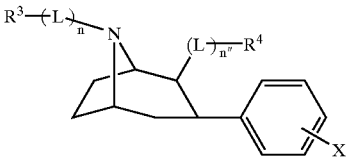

(3)

wherein $R^1$ and $R^2$ are as defined above.

Another aspect of the present invention is directed to a process for synthesizing a phenyltropane derivative represented by the formula (4):

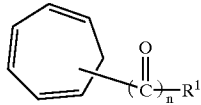

(4)

wherein $R^3$ is a group selected from the group consisting of an unsubstituted alkyl group, a substituted alkyl group, an unsubstituted aralkyl group, a substituted aralkyl group and a chelating group capable of forming a complex together with a radioactive transition metal; $R^4$ is a group selected from the group consisting of an alkyl ester group and a chelating group capable of forming a complex together with a radioactive transition metal; L is a methylene chain of 1 to 4 carbon atoms as a connecting portion; n' and n" are independently an integer of 1 or 0; and X is a hydrogen atom, an alkyl group, an alkoxy group, or a halogen atom or its radioisotope, which process uses as an intermediate for the synthesis an anhydroecgonine derivative of the formula (3) obtained by reacting the above-mentioned cycloheptatriene derivative with a primary amine, a salt thereof or ammonia.

The present invention has made it possible to provide a process for synthesizing an anhydroecgonine derivative useful as an intermediate for synthesis of a tropane derivative, without using cocaine as a starting material, and a process for synthesizing a tropane derivative by using said anhydroecgonine derivative as an intermediate for the synthesis. Consequently, as compared with conventional processes for synthesizing a phenyltropane derivative, the present invention makes it possible to obtain efficiently a physiologically active phenyltropane derivative by synthesizing a phenyltropane derivative by a shortened synthetic procedure without using cocaine, ecgonine or the like as an intermediate, and carrying out optical resolution by HPLC in combination with the synthesis. For example, it has become possible to obtain an optically active phenyltropane derivative such as methyl [1R-(2-exo,3-exo)]-3-(4-iodophenyl)-8-methyl-8-azabicyclo-[3.2.1]octane-2-carboxylate, methyl [1R-(2-exo, 3-exo)]-8-(3-fluoropropyl)-3-(4-iodophenyl)-8-azabicyclo-[3.2.1]octane-2-carboxylate, [1R-(2-exo,3-exo)]-2-[[[3-(4-chlorophenyl)-8-methyl-8-azabicyclo[3.2.1]oct-2-yl]methyl](2-sulfanilethyl)amino]ethyl]amino]-ethanethiol salt or the like by a shortened synthetic procedure by using a cycloheptatriene derivativer as a starting material, using as an intermediate an anhydroecgonine derivative having a desirable substituent suitable for purposes introduced thereinto at the N-8 position, and carrying out optical resolution in a proper stage of the synthesis of the phenyltropane derivative. These compounds thus obtained have the same tropane skeleton as that of a cocaine derivative and are effectively used as a radioactive tracer for mapping of brain dopamine transporters by SPECT or PET imaging in nuclear medicine.

DETAILED DESCRIPTION OF THE INVENTION

The anhydroecgonine derivative obtainable by the synthetic process of the present invention is synthesized without using cocaine as a starting material, and it is useful as an intermediate for synthesis of cocaine analogous which has the same tropane skeleton as that of cocaine, i.e., the basic ring structure of cocaine and has the same optical activity as in the case of deriving the analogous compound from natural (−)-cocaine.

Reaction scheme B

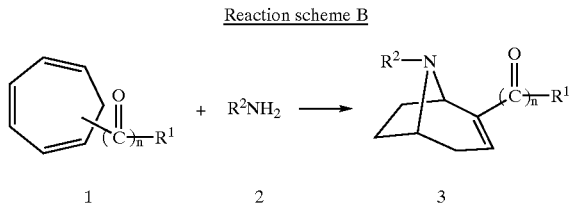

The anhydroecgonine derivative obtainable by the synthetic process of the present invention can be synthesized by the process shown in the above reaction scheme B. The cycloheptatriene derivative 1 has four isomers α, β, γ and δ relative to the position of the substituent, and any of them may be used. Cycloheptatrienecarbonitrile of the above formula 1 wherein n is 0 and $R^1$ is a cyano group in the substituent is a preferable cycloheptatriene derivative. Cycloheptatrienecarbonitrile can be obtained by a well-known process. For example, 2,4,6-cycloheptatriene-1-carbonitrile, an isomer of cycloheptatrienecarbonitrile, can be obtained as an orange oil by dissolving tropylidene in carbon tetrachloride, brominating tropylidene by dropwise addition of bromine to obtain cycloheptatrienilium bromide, and the resulting compound was allowed to react with an aqueous potassium cyanide solution with heating (Doeling, W. von E., et al., J. Am. Chem. Soc., 79, 352–356(1957)). The primary amine, ammonia or the like, which is allowed to react with the above-mentioned cycloheptatriene derivative, is also a well-known compound synthesized by a per se well-known process.

In the above reaction scheme B, either the primary amine 2 or a salt thereof may be used. The substituent $R^2$ of the primary amine is selected from the group consisting of a hydrogen atom, an unsubstituted alkyl group, a substituted alkyl group, an unsubstituted aralkyl group, a substituted aralkyl group, etc. Specific examples of the unsubstituted alkyl group are alkyl groups of 1 to 6 carbon atoms, such as methyl, ethyl, propyl, isopropyl, butyl, tert-butyl, sec-butyl, pentyl, 2-pentyl, 3-pentyl, isopentyl, neopentyl, hexyl, etc. The substituted alkyl group includes monofluoro-substituted alkyl groups. Specific examples thereof are monofluoroethyl group, monofluoropropyl group, etc. The unsubstituted aralkyl group includes, for example, aralkyl groups of 7 to 10 carbon atoms, such as benzyl, phenethyl, phenylpropyl, phenylbutyl, etc. The substituted aralkyl group includes fluorobenzyl group, methylbenzyl group, etc.

As the anhydroecgonine derivative 3, various derivatives can be synthesized by properly selecting the substituent of the cycloheptatriene derivative 1 and the substituent $R^2$ of the primary amine 2. In the formula 3, $R^1$ is a cyano group in the case of n being 0, and $R^1$ is selected from an alkyl group and an aralkyl group in the case of n being 1. Specific examples of the alkyl groups are alkyl groups of 1 to 6 carbon atoms, such as methyl, ethyl, propyl, isopropyl, butyl, tert-butyl, sec-butyl, pentyl, 2-pentyl, 3-pentyl, isopentyl, neopentyl, hexyl, etc. The aralkyl groups include aralkyl groups of 7 to 10 carbon atoms, such as benzyl, phenethyl, phenylpropyl, phenylbutyl, etc.

A base such as sodium hydroxide, potassium hydroxide or the like is used in the reaction of the cycloheptatriene derivative with the primary amine or ammonia. The primary amine or ammonium may be used in itself as the base. When a salt of the primary amine is reacted, sodium hydroxide or potassium hydroxide is used as required. The reaction is carried out in a solvent such as water, methanol, ethanol, dioxane or the like at a reaction temperature of 80 to 150° C. The anhydroecgonine derivative 3 thus obtained can be used as an intermediate in a modified process for synthesizing 2β-carbomethoxy-3β-(4-iodophenyl)tropane (methyl [1R-(2-exo,3-exo)]-3-(4-iodophenyl)-8-methyl-8-azabicyclo[3.2.1]octane-2-carboxylate), N-(3-fluoropropyl)-2β-carbomethoxy-3β-(4-iodophenyl)-nortropane (methyl [1R-(2-exo,3-exo)]-8-(3-fluoropropyl)-3-(4-iodophenyl)-8-azabicyclo[3.2.1]-octane-2-carboxylate) or the like, which is useful as a radioactive tracer for use in SPECT or PET for mapping dopamine transporters in brain, without producing cocaine as an intermediate.

The reaction scheme C shown below is an example of reaction scheme for synthesizing an anhydroecgonine derivative (the formula 3) and a phenyltropane derivative (the formula 6) without producing cocaine as an intermediate. In detail, the reaction scheme C is a scheme in which methyl (1RS)-8-methyl-8-azabicyclo-[3.2.1]oct-2-ene-2-carboxylate (7:(1RS)-AECG ; such an abbreviation of a compound name is hereinafter described in a parenthesis and properly used) is synthesized, and then a fluoropropyl group is introduced thereinto at the N-8 position to synthesize methyl [1RS-(2-exo,3-exo)]-8-(3-fluoropropyl)-3-(4-iodophenyl)-8-azabicyclo[3.2.1]octane-2-carboxylate (12: (1RS)-β-CIT-FP). Specifically, 2,4,6-cycloheptatriene-1-carbonitrile (4:CHT-CN) is allowed to react with methylamine in methanol solvent in the presence of sodium hydroxide to obtain (1RS)-8-methyl-8-azabicyclo[3.2.1]oct-2-ene-2-carbonitrile (6:(1RS)-AECG-CN). The cyano group of this compound is hydrolyzed and then converted to a methyl ester group to obtain methyl (1RS)-8-methyl-8-azabicyclo[3.2.1]oct-2-ene-2-carboxylate (7:(1RS)-AECG), which is allowed to react with phenylmagnesium bromide (PhMgBr) by a well-known method to obtain methyl [1RS-(2-exo,3-exo)]-3-phenyl-8-methyl-8-azabicyclo[3.2.1]octane-2-carboxylate (8:(1RS)-β-CPT). The tropane portion of this compound is converted to nortropane at the N-8 position, followed by substitution by a fluoropropane group at the N-8 position, whereby (1RS)-β-CIT-FP 12 can be obtained. optically active (1R)-β-CIT-FP can be obtained by optical resolution of (1RS)-β-CIT-FP 12 or by subjecting (1RS)-nor-β-CIT 11 to optical resolution to obtain an optically active substance in the course of the synthesis and continuing reactions shown in Reaction scheme C.

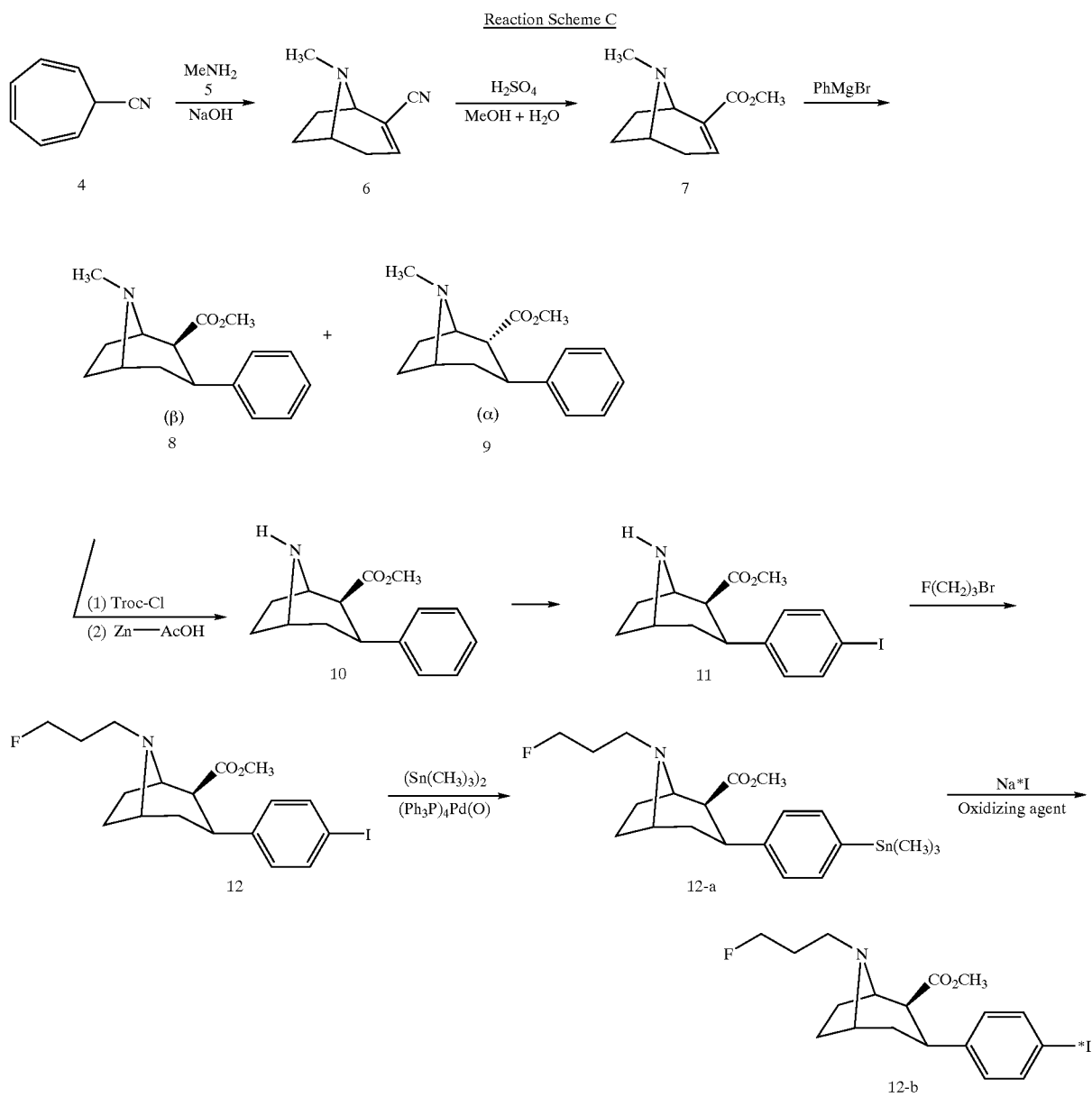

Reaction Scheme C

According to the present inventive synthetic process using an anhydroecgonine derivative as an intermediate, it becomes possible to further shorten the procedure for synthesizing a phenyltropane derivative shown in the reaction scheme C. In detail, as the primary amine used in the first reaction step, i.e., the reaction of the cycloheptatriene derivative with the primary amine, there is properly chosen a primary amine having a substituent that the phenyltropane derivative is desired to have at the N-8 position, whereby the steps after the first reaction step, such as the introduction of the substituent can be omitted, so that the whole synthesis procedure can be shortened. An explanation is made below by giving a specific example. As shown in the reaction scheme D exhibited below, CHT-CN is allowed to react with fluoropropylamine at first to synthesize methyl [1RS-(2-exo, 3-exo)]-8-(3-fluoropropyl)-8-azabicyclo[3.2.1]-oct-2-ene-2-carbonitrile (13:(1RS)-AECG-CN-FP) having a fluoropropyl group introduced thereinto at the N-8 position, which is converted to methyl [1RS-(2-exo,3-exo)]-8-(3-fluoropropyl)-8-azabicyclo[3.2.1]oct-2-ene-2-carboxylate (14:(1RS)-AECG-FP) and then methyl [1RS-(2-exo,3-exo)]-8-(3-fluoropropyl)-3-phenyl-8-azabicyclo[3.2.1] octane-2-carboxylate (15:(1RS)-β-CPT-FP). Thus, the steps such as the conversion to a nortropane and the substitution by a fluoropropyl group are unnecessary after the synthesis of (1RS)-AECG-CN-FP, so that the whole procedure for synthesizing the final desired compound (1RS)-β-CIT-FP can be shortened to 4 reaction steps from the 6 reaction steps of the procedure for synthesizing (1RS)-β-CIT-FP shown in the reaction scheme C.

Reaction scheme D

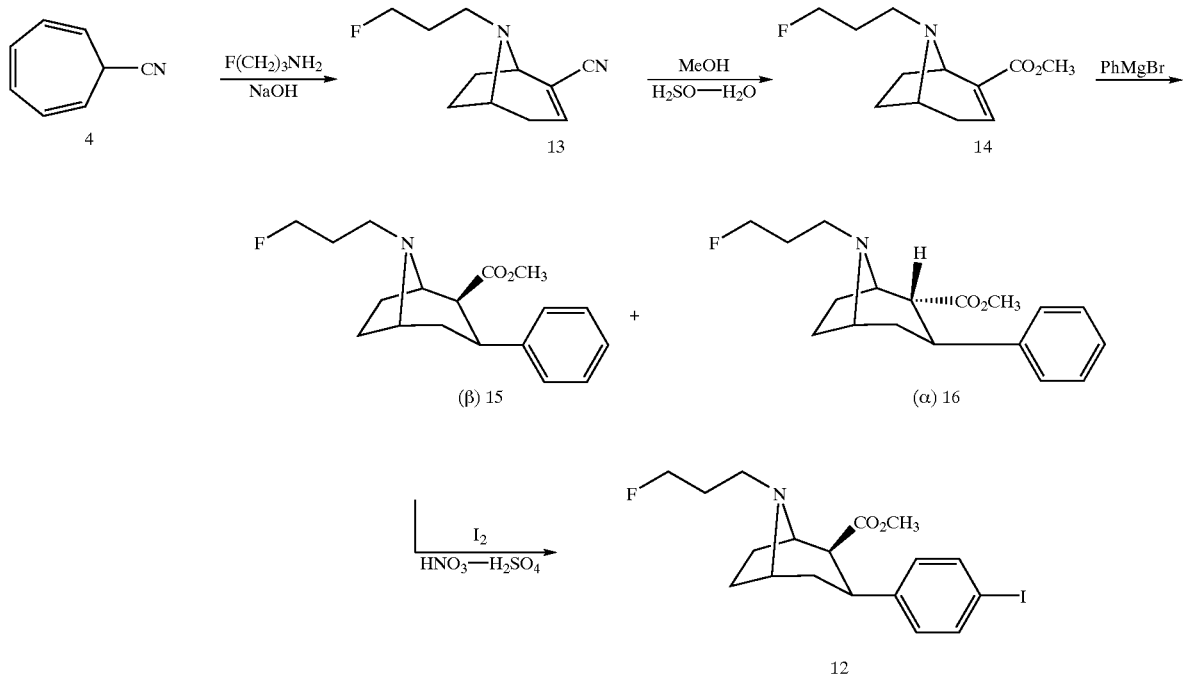

In the reaction scheme D, the cyano group of (1RS)-AECG-CN-FP obtained by the reaction of CHT-CN with fluoropropylamine is converted to a methyl ester group before the Grignard reaction. On the other hand, the reaction scheme E exhibited below shows that the conversion to a methyl ester group can be carried out after the Grignard reaction. That is, the following is also possible: (1RS)-AECG-CN-FP is allowed to react with a Grignard reagent to obtain [1RS-(2-exo,3-exo)]-8-(3-fluoropropyl)-3-phenyl-8-azabicyclo[3.2.1]octane-2-carbonitrile (17:(1RS)-β-CPT-CN-FP), and then (1RS)-β-CIT-FP is obtained via (1RS)-β-CPT-FP. A useful optically active substance such as (1R)-β-CIT-FP can be obtained depending on purposes, by carrying out optical resolution in a proper stage in the reaction scheme.

Reaction scheme E

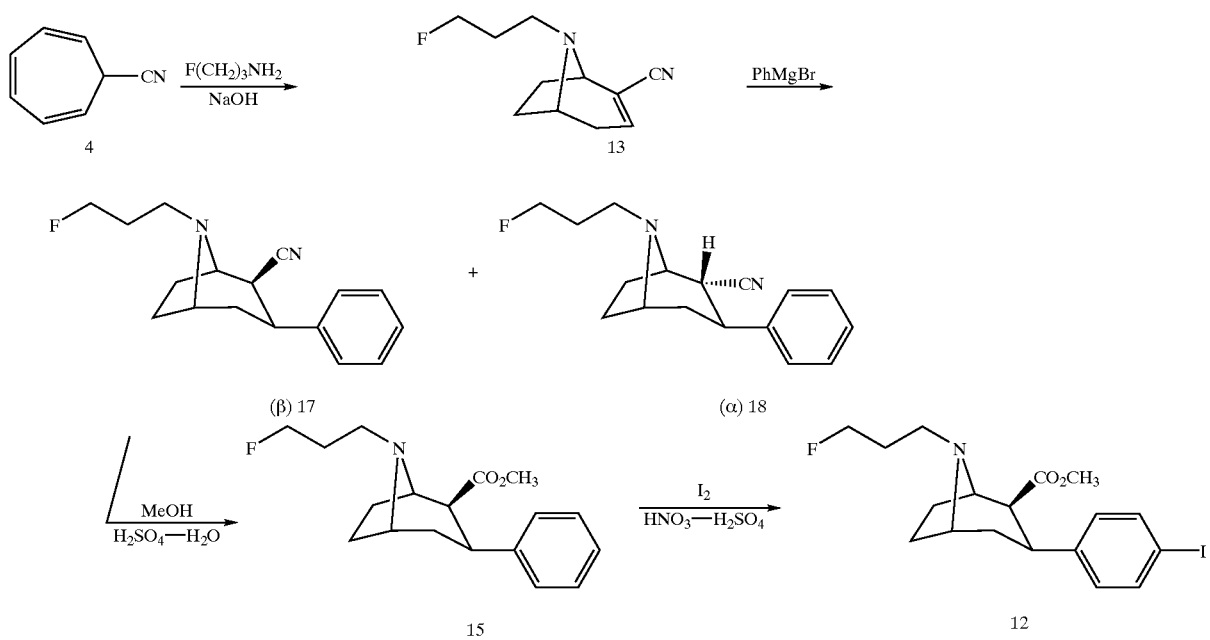

The optically active (1R)-β-CIT-FP obtained in the manner described above is used as a radioactive imaging agent after being labeled with a radioisotope (Iodine-123 or Iodine-131) used as a substituent for the iodine atom of the 4-iodophenyl group. The labeling can be conducted by a well-known method such as a method in which a precursor for iodine labeling obtained by replacing the iodine atom with a trialkyltin group is allowed to react with sodium iodide of Iodine-123 or Iodine-131 in the presence of an oxidizing agent. The scheme C shows, as a specific example of the labeling, a case where β-CIT-FP is converted to a trimethyltin compound 12-a, i.e., a precursor for iodine labeling, and then this compound is converted to a radioiodinated compound 12-b. Such a method for labeling by iodiodestannylation which gives a carrier free radioiodinated compound is widely adopted for synthesizing a radioactive-iodine-labeled compound of a substance capable of binding to receptors and is adopted for labeling a phenyltropane derivative obtained according to the present invention, with radioactive iodine.

When the phenyltropane compound is labeled with a radioisotope, a halogen atom (an iodine, bromine or fluorine atom) attached to the phenyl group at the 3-position of the phenyltropane compound may be replaced with a radioisotope as described above, or the substituent at the 2-position or N-8 position of the tropane ring may be labeled with a radioisotope. The following is also possible: the substituent at the 2-position or N-8 position of the tropane ring is replaced with a chelating group, and the chelating group is allowed to form a complex together with a radioactive transition metal nuclide useful for SPECT imaging, such as Technetium-99m, Rhenium-186, Rhenium-188 or the like to obtain a phenyltropane derivative labeled with the radioactive transition metal.

The chelating group for the radioactive transition metal includes diaminodithiols, monoamidomonoaminodithiols, diamidodithiols, triamidothiols, etc. Specific examples of the chelating group are diaminodithiols such as N,N'-bis(2-mercaptoethyl)-ethylenediamine, 2,2,9,9-tetramethyl-4,7-diaza-1,10-decanethiol, etc.; monoamidomonoaminodithiols such as N-2-mercaptoethyl-2-mercaptoethylaminoacetamide, N-(2-mercaptoethyl)aminoethyl-2-mercaptoacetamide, etc.; diamidodithiols such as 1,2-ethylenebis(2-mercaptoacetamide), etc.; and triamidothiols such as mercaptoacetylglycylglycylglycine, etc.

The reaction scheme F exhibited below shows an example of procedure for synthesizing a phenyltropane derivative ([1RS-(2-exo,3-exo)]-2-[[2-[[[3-(4-chlorophenyl)-8-methyl-8-azabicyclo[3.2.1]oct-2-yl]methyl](2-sulfanilethyl)amino]ethyl]amino]-ethanethiol trifluoroacetate 23) which has a diaminodithiol type chelating group introduced thereinto. That is, using CHT-CN as a starting material, methyl [1RS-(2-exo,3-exo)]-3-(4-chlorophenyl)-8-methyl-8-azabicyclo[3.2.1]octane-2-carboxylate (20:(1RS)-β-CCIT) is synthesized via (1RS)-AECG-CN and (1RS)-AECG, and then there can be synthesized a phenyltropane derivative ([1RS-(2-exo,3-exo)]-2-[[2-[[[3-(4-chlorophenyl)-8-methyl-8-azabicyclo[3.2.1]oct-2-yl]methyl](2-sulfanilethyl)-amino]ethyl]amino]ethanethiol trifluoroacetate 23) which has a diaminodithiol type chelating group as a substituent at the 2-position.

Reaction scheme F

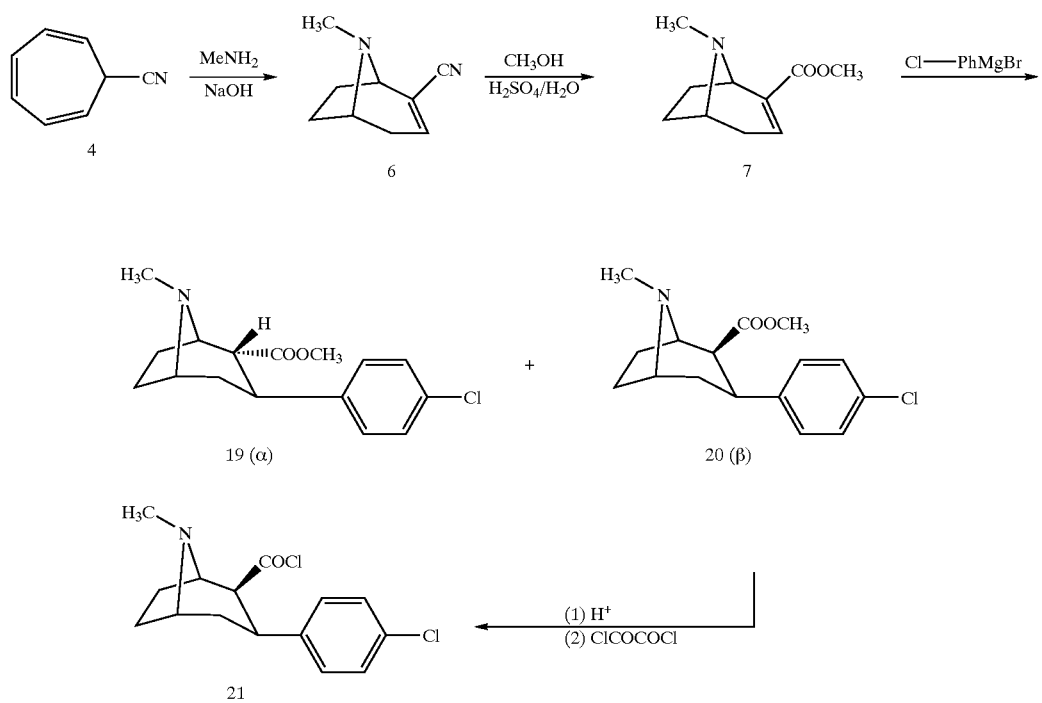

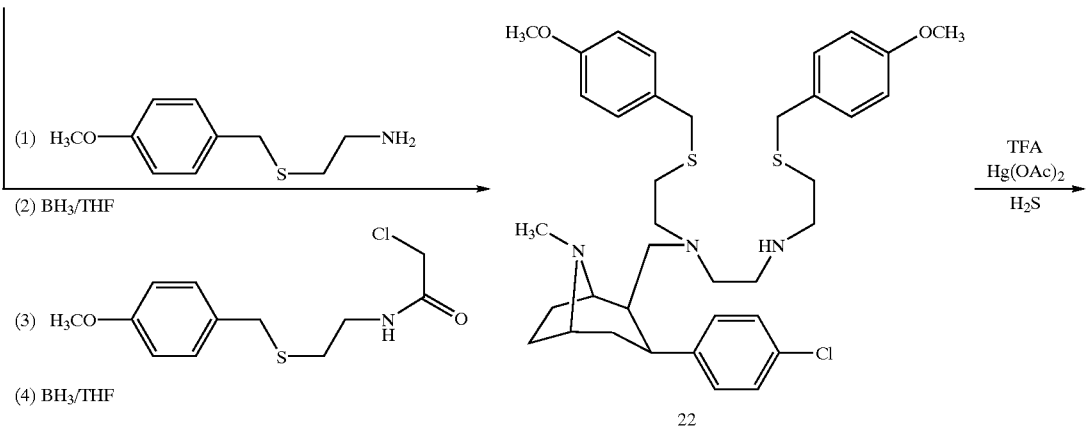

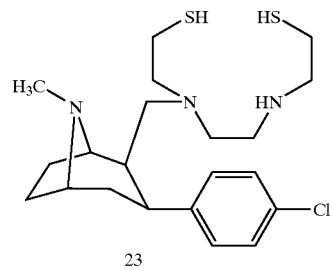

The following reaction scheme G shows that the whole procedure for synthesizing a phenyltropane derivative capable of forming a chelate can be shortened by introducing a chelating group into the 2-position of the tropane skeleton of (1RS)-AECG-CN without esterifying the cyano group of (1RS)-AECG-CN. Thus, the procedure for synthesizing the final product, i.e., the phenyltropane derivative capable of forming a chelate can be shortened by using the anhydroecgonine derivative according to the present invention.

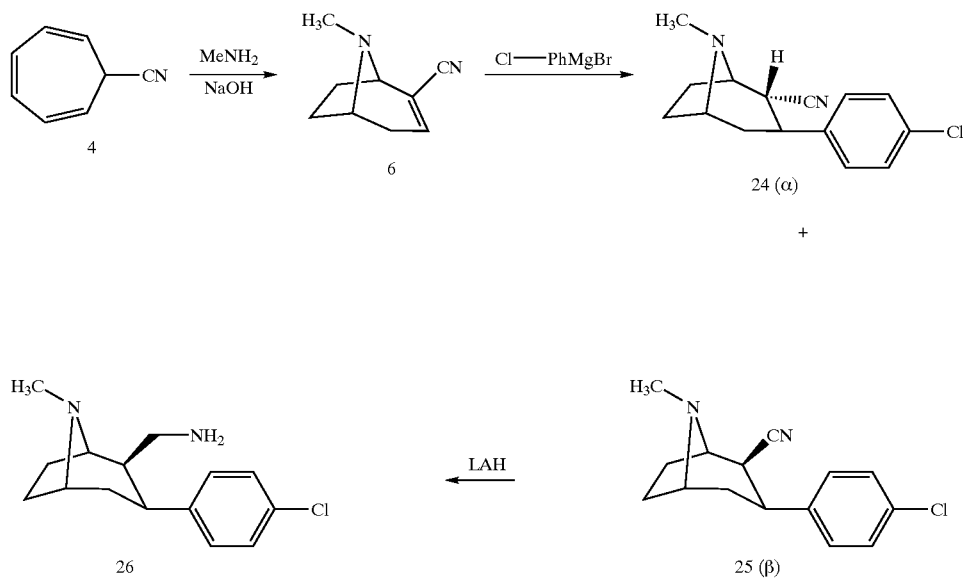

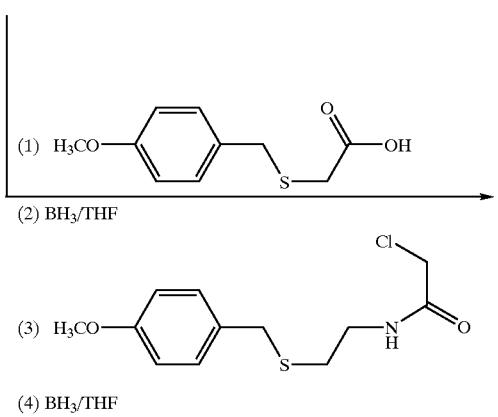
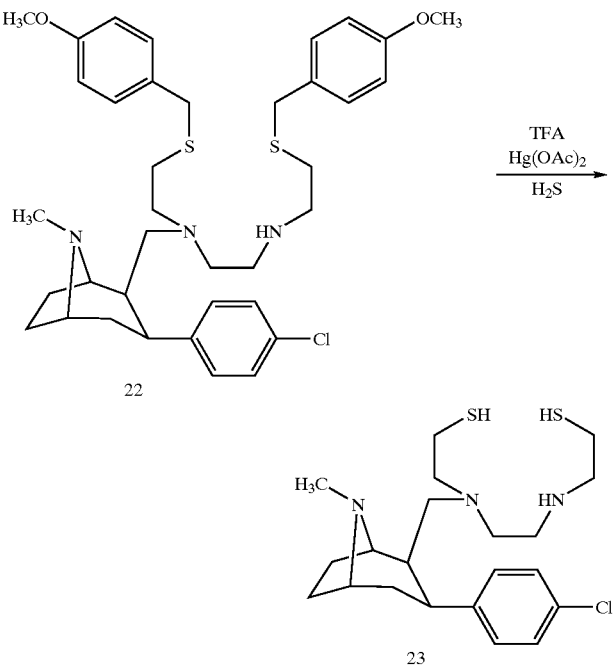

EXAMPLES

The present invention is illustrated below in further detail with the following examples, which should not be construed as limiting the scope of the invention. Methods for measurement for the substances obtained in the examples, and the like are as follows.

(1) Measurement of an NMR Spectrum:

NMR spectra were measured by means of JEOL GSX270 (mfd. by Nippon Denshi Co., Ltd.).

(2) HPLC:

There were used a HPLC system PU986, UV970 (mfd. by Nippon Bunko Co., Ltd.), Chromatocorder 21 (System Instrument), SUMIPAX ODS column type A211, and a mixed solvent of methanol, water and triethylamine.

(3) Measurement of Optical Rotation:

SEPA-200 (mfd. by Horiba Seisakusho Co., Ltd.) was used as a polarimeter, and chloroform was used as a solvent.

In each example, the compound numbers described in the synthesis scheme and the abbreviations of names of the compounds are described side by side. The abbreviations of names of the compounds are properly used. Examples 1 to 7 are based on the reaction scheme C, Examples 10 to 13 on the reaction scheme D, Examples 14 and 15 on the reaction scheme E, Examples 16 to 22 on the reaction scheme F, and Examples 23 and 24 on the reaction scheme G.

Example 1

Synthesis of (1RS)-8-methyl-8-azabicyclo-[3.2.1] oct-2-ene-2-carbonitrile (6:(1RS)-AECG-CN)

In 2 ml of methanol was dissolved 0.5 g (4.27 mmol) of 2,4,6-cycloheptatriene-1-carbonitrile (4: CHT-CN). A solution of 171 mg (4.27 mmol) of sodium hydroxide in 5 ml of methanol and then 3 ml (about 38 mmol) of 40% methanolic solution of methylamine were added thereto, and the resulting mixture was stirred with heating at 125° C. for 10 hours in a sealed vessel. After standing at room temperature, the methanol was evaporated and the residue was adjusted to pH 2 with 1N sulfuric acid solution, followed by extraction with chloroform (No. of run: 1) or ether (No. of run: 2 to 5) (separation into an organic layer 1 and an aqueous layer 1). The aqueous layer 1 was neutralized with 4N sodium hydroxide solution, followed by extraction with chloroform (No. of run: 1) or ether (No. of run: 2 to 5) (separation into an organic layer 2 and an aqueous layer 2). The organic layer 2 was dried and then the solvent was evaporated therefrom to obtain 0.458 g of a brown oil (1RS)-AECG-CN (yield: 70%).

$^1$H-NMR(CDCl$_3$)ppm: 1.5–1.7(m, 2H), 1.8(dd, 1H), 1.9–2.2(m, 2H), 2.38(s, 3H, NCH$_3$), 2.5–2.6(bd, 1H), 3.3(t, 1H), 3.4(d, 1H), 6.56(dt, 1H, =CH—).

Reaction was carried out in the same manner as above except for varying the base, the amount of methylamine, the reaction temperature, the reaction time and the like. The results obtained are summarized in Table 1.

TABLE 1

| No. of run | CHT-CN (mmol) | NaOH or KOH (mmol) | MeNH$_2$ (mmol) | Temperature (° C.) | Time (Hr) | Yield (%) |
|---|---|---|---|---|---|---|
| 1 | 4.27 | 4.27(NaOH) | 38 | 125 | 10 | 70 |
| 2 | 4.27 | 4.62(KOH) | 39 | 118 | 10 | 87 |
| 3 | 5.72 | 5.68(KOH) | 103 | 120 | 10 | 80 |
| 4 | 21.0 | 20.7(KOH) | 452 | 90 | 3 | 81 |
| 5 | 5.98 | — | 54 | 125 | 3 | 61 |

Example 2

Synthesis of methyl (1RS)-8-methyl-8-azabicyclo [3.2.1]oct-2-ene-2-carboxylate (7:(1RS)-AECG; dl-anhydroecgonine methyl ester)

In 2.3 ml of 95% methanol solution was dissolved 0.727 g (4.91 mmol) of the (1RS)-AECG-CN synthesized in Example 1, followed by adding thereto 1.2 ml of concentrated sulfuric acid, and the resulting mixture was stirred with heating at 110° C. for 6 hours. After completion of the reaction, the methanol was evaporated and the residue was neutralized with saturated sodium hydrogencarbonate solution, followed by extraction with ethyl acetate. The organic layer was dried and then distilled to remove the solvent, whereby 0.41 g of (1RS)-AECG was obtained as a brown oil (yield: 46%).

$^1$H-NMR(CDCl$_3$)ppm: 1.4–1.6(m, 1H), 1.7–1.9(m, 2H), 2.0–2.3(m, 2H), 2.35(s, 3H, NCH$_3$), 2.56–2.69(d, 1H), 3.2–3.3(m, 1H), 3.7–3.8(m, 1H), 3.74(s, 3H, COOCH$_3$), 6.82(dt, 1H, =CH—).

Example 3

Synthesis of methyl [1RS-(2-exo,3-exo)]-3-phenyl-8-methyl-8-azabicyclo[3.2.1]octane-2-carboxylate (8:(1RS)-β-CPT)

In a two-necked flask, 50 ml of anhydrous ether was placed under argon gas and cooled to −40° C. Then, 1.8 ml of 3M ethereal solution of phenylmagnesium bromide was added thereto and the resulting mixture was stirred at −40° C. for 30 minutes. A solution in 50 ml of anhydrous ether of 0.492 g (2.72 mmol) of the (1RS)-AECG synthesized in Example 2 was added dropwise thereto, followed by stirring at −40° C. for 4 hours. Thereafter, 20 ml of 1M ethereal solution of hydrochloric acid was added thereto and stirred for 5 minutes. The resulting mixture was cooled to room temperature by adding ice water with further stirring, followed by extraction with ether (separation into an organic layer 1 and an aqueous layer 1). The aqueous layer 1 was adjusted to pH 8 with concentrated aqueous ammonia, followed by extraction with ether and chloroform (separation into an organic layer 2 and an aqueous layer 2). The organic layer 2 was dried and then distilled to remove the solvent, whereby 0.78 g in total of a light-yellow oil was obtained. The oil was purified by silica gel column chromatography (flash chromatography, eluent: hexane/ethyl acetate=20/1 to 1/1) to obtain 0.296 g of (1RS)-β-CPT as a light-yellow oil (yield: 42%). In the reaction described above, methyl [1RS-(2-endo,3-exo)]-3-phenyl-8-methyl-8-azabicyclo[3.2.1]octane-2-carboxylate (9:(1RS)-α-CPT), i.e., a stereoisomer of the above-mentioned (1RS)-β-CPT was produced as a by-product. This by-product was recovered, and the compounds thus obtained were identified by proton NMR measurement. The values obtained for each compound by the proton NMR measurement were assigned with reference to the values described in literature (Zheng et al., Nucl. Med. Biol., 23, 981–986(1996)). The yields of (1RS)-β-CPT and (1RS)-α-CPT were 32% and 16%, respectively, for different batch.

The assignment of the values obtained for each compound by the proton NMR measurement were as follows.

$^1$H-NMR measurement results for (1RS)-β-CPT:

$^1$H-NMR(CDCl$_3$)ppm: 1.5–2.2(m, 5H), 2.25(s, 3H, NCH$_3$), 2.62(t, 1H), 2.92(m, 2H), 3.38(m, 1H), 3.48(s, 3H, COOCH$_3$), 3.57(m, 1H), 7.1–7.3(m, 5H, Ar—H).

$^1$H-NMR Measurement Results for (1RS)-α-CPT:

$^1$H-NMR(CDCl$_3$)ppm: 1.5–2.2(m, 6H), 2.42(s, 3H, NCH$_3$), 3.1–3.16(m, 2H), 3.25(m, 1H), 3.41(m, 1H), 3.50(s, 3H, COOCH$_3$), 7.1–7.3(m, 5H, Ar—H).

Example 4

Synthesis of methyl [1RS-(2-exo,3-exo)]-3-phenyl-8-azabicyclo[3.2.1]octane-2-carboxylate (10:(1RS)-nor-β-CPT)

In 1.2 ml of 2,2,2-trichloroethyl trichloroformate (Troc-Cl) was dissolved 0.293 g (1.13 mmol) of the (1RS)-β-CPT synthesized in Example 3. The resulting solution was stirred with heating at 120° C. for 1 hour. Since the disappearance of the staring material was revealed by thin-layer chromatography analysis, the excess Troc-Cl was distilled off under reduced pressure to obtain 0.55 g of a brown oil. In 10 ml of 95% acetic acid solution was dissolved 0.55 g of the oil, followed by adding thereto 1.2 g of zinc powder, and the resulting mixture was stirred at room temperature for 18 hours. The reaction solution was filtered by suction and the residue was washed with 95% acetic acid solution. The filtrate thus obtained was extracted with ether. The aqueous layer was neutralized with 2N sodium hydroxide solution and extracted with chloroform. The resulting organic layer was washed with saturated aqueous sodium chloride solution, dried and then distilled to remove the solvent, whereby 0.192 g of (1RS)-nor-β-CPT was obtained as a light-yellow oil (yield: 69%).

Example 5

Synthesis of methyl [1RS-(2-exo,3-exo)]-3-(4-iodophenyl)-8-azabicyclo[3.2.1]octane-2-carboxylate (11:(1RS)-nor-β-CIT)

In 4 ml of acetic acid were dissolved 0.32 g (1.31 mmol) of the (1RS)-nor-β-CPT synthesized in Example 4 and 0.33 g (1.31 mmol) of iodine. Then, 0.8 ml of concentrated sulfuric acid and 0.8 ml of concentrated nitric acid were added dropwise thereto and the resulting mixture was stirred with heating at 55° C. for 2 hours in a sealed vessel. After completion of the reaction, the reaction solution was cooled to room temperature by adding ice water, and then adjusted to pH 8 with concentrated aqueous ammonia. This reaction solution was extracted with chloroform, and the organic layer was washed with 10% sodium disulfite solution or a sodium thiosulfate solution. The washed organic layer was dried and then distilled to remove the solvent, whereby 0.286 g of a crude product was obtained. The crude product was purified by silica gel column chromatography (eluent: chloroform/methanol=20/1) to obtain 0.225 g of (1RS)-nor-β-CIT as a light-yellow or white solid (yield: 46%).

$^1$H-NMR(CDCl$_3$)ppm: 1.6–2.3(m, 5H), 2.39(dt, 1H), 2.73 (d, 1H), 3.18(m, 1H), 3.40(s, 3H, COOCH$_3$), 3.7–3.8(m, 2H), 6.95, 7.60(d, d, 4H, Ar—H).

Example 6

Synthesis of methyl [1RS-(2-exo,3-exo)]-8-(3-fluoropropyl)-3-(4-iodophenyl)-8-azabicyclo[3.2.1]-octane-2-carboxylate (12:(1RS)-β-CIT-FP)

In 9 ml of toluene was dissolved 0.13 g (0.35 mmol) of the (1RS)-nor-β-CIT obtained in Example 5. Then, 0.2 ml of 1-bromo-3-fluoropropane and 0.2 ml of triethylamine were added thereto and the resulting mixture was heated under reflux for 6.5 hours. After completion of the reaction, the desired compound was extracted with ether to obtain 0.174 g of a brown oil. The oil was purified by silica gel column chromatography (eluent: chloroform) to obtain 0.125 g of (1RS)-β-CIT-FP as a light-yellow oily or solid (yield: 83%).

$^1$H-NMR(CDCl$_3$)ppm: 1.5–2.2(m, 7H), 2.37(dt, 2H), 2.53 (dt, 1H), 2.84–3.02(m, 2H), 3.38(m, 1H), 3.50(s, 3H, COOCH$_3$), 3.68(m, 1H), 4.43, 4.61(t, t, 2H, F—CH$_2$—), 7.01, 7.58(d, d, 4H, Ar—H). $^{13}$C-NMR(CDCl$_3$)ppm: 26.0, 29.9, 30.2, 33.8, 49.2, 50.9, 52.6, 61.3, 63.1, 81.0, 83.3, 90.9, 129.4, 136.8, 143.0, 171.7.

Example 7

Synthesis of methyl [1RS-(2-exo,3-exo)]-8-(3-fluoropropyl)-3-(4-trimethylstannylphenyl)-8-azabicyclo[3.2.1]octane-2-carboxylate 12-a In 2 ml of toluene were dissolved 83 mg (0.193 mmol) of the (1RS)-β-CIT-FP obtained in Example 6, 0.15 g (0.46 mmol) of hexamethylditin and 3 mg (2.6 μmol) of tetrakis (triphenylphosphine)palladium(0), and the resulting solution was refluxed for 6 hours. After completion of the reaction, the reaction mixture was filtered and the solvent was evaporated from the filtrate. The resulting residue was purified by silica gel column chromatography (eluent: ethyl acetate) to obtain 66 mg of methyl [1RS-(2-exo,3-exo)]-8-(3-fluoropropyl)-3-(4-trimethylstannylphenyl)-8-azabicyclo[3.2.1]octane-2-carboxylate 12-a as a colorless oil (yield: 73%).

$^1$H-NMR(CDCl$_3$)ppm: 0.24 (s, 9H, SnMe$_3$), 1.6–2.2(m, 7H), 2.37(dt, 2H), 2.58(dt, 1H), 2.7–3.1(m, 2H), 3.38(m, 1H), 3.48(s, 3H, COOCH$_3$), 3.68(m, 1H), 4.44, 4.61(t, t, 2H, F—CH$_2$—), 7.20, 7.42(d, d, 4H, Ar—H).

As shown in the reaction scheme C, the compound 12-a obtained in Example 7 is used as a precursor of a radioactive-iodine-labeled compound 12-b. Also when an optically active substance is used, it is possible to synthesize a precursor for iodine labeling in the same manner as above and label the precursor with radioactive iodine.

Example 8

Optical Resolution

The (1RS)-AECG, (1RS)-β-CPT, (1RS)-nor-β-CIT and (1RS)-β-CIT-FP obtained in Examples 2, 3, 5 and 6, respectively, were subjected to analysis for optical resolution by using a column for separation of optical isomers [column: CHIRALCEL OD4.6 mm I.D.×250 mm (mfd. by Daicel Kagaku Kogyo Co., Ltd.), eluent: hexane/2-propanol=95/5, flow rate: 1 ml/min, UV 254 nm detection]. The retention time of isomers of each compound is shown in Table 2.

TABLE 2

Retention time of isomers of each compound

| Compound | Retention time (min.) | | Resolution (α) |
|---|---|---|---|
| 1RS-AECG | 5.6 | 7.3 | 1.30 |
| 1RS-β-CPT | 6.1 | 11.0 | 1.80 |
| 1RS-nor-β-CIT | 10.7 | 13.5 | 1.26 |
| 1RS-β-CIT-FP | 5.6 | 6.4 | 1.19 |

At present, levorotatory optical isomer of β-CIT-FP is desired as a useful final compound. However, since the resolution of isomers of each of (1RS)-AECG, (1RS)-β-CPT and (1RS)-nor-β-CIT, i.e., compounds synthesized prior to the synthesis of (1RS)-β-CIT-FP is higher than the resolution of isomers of (1RS)-β-CIT-FP, optical resolution is preferably carried out in a proper stage of the synthesis of (1RS)-β-CIT-FP in view of the yields of the compounds, and the like. In the case described above, it is preferable to obtain optically active (1R)-nor-β-CIT by optical resolution of (1RS)-nor-β-CIT and then synthesize (1R)-β-CIT-FP as an optically active substance.

Example 9

Measurement of Optical Purity and Optical Rotation

The crude product of (1RS)-nor-β-CIT synthesized in Example 5 was subjected to optical resolution in the same manner as in Example 8 to separate a fraction A having a retention time of 10.7 minutes and a fraction B having a retention time of 13.5 minutes. The purity, optical purity, optical rotation and specific rotation of each of the fractions were measured. The results obtained are shown in Table 3. The fraction A was dextrorotatory and the fraction B was levorotatory. Thus, the fraction B was (1R)-nor-β-CIT having the same absolute configuration as that of cocaine.

TABLE 3

| Fraction | Purity | Optical purity | Optical rotation α | Specific rotation $[\alpha]_D^{22}$ | Note |
|---|---|---|---|---|---|
| A | 97% | 97.6% cc | 0.712° | 78° | C = 0.913, CHCl$_3$ Cell length = 10 cm |
| B | 93% | 95.8% cc | −0.131° | −78° | C = 0.167, CHCl$_3$ Cell length = 10 cm |

Values Described in Literature:
$[\alpha]_D^{25}$ −67.4°, C=1, CHCl$_3$ (U.S. Pat. No. 5,310,912)

Example 10

Synthesis of [1RS-(2-exo,3-exo)]-8-(3-fluoropropyl)-8-azabicyclo[3.2.1]oct-2-ene-2-carbonitrile (13:(1RS)-AECG-CN-FP)

In 2 ml of methanol was dissolved 0.5 g (4.27 mmol) of CHT-CN. A solution of 0.171 g (4.28 mmol) of sodium hydroxide in 5 ml of methanol and then 3-fluoropropylamine (about 38 mmol) were added thereto, and the resulting mixture was stirred with heating at 125° C. for 3 hours in a sealed vessel. After standing at room temperature, the methanol was evaporated and the residue was adjusted to pH 2 with 1N sulfuric acid solution and extracted with chloroform. The aqueous layer was neutralized with 4N sodium hydroxide solution and extracted with ether. The resulting organic layer was dried and then the solvent was evaporated therefrom to obtain (1RS)-AECG-CN-FP.

Example 11

Synthesis of methyl [1RS-(2-exo,3-exo)]-8-(3-fluoropropyl)-8-azabicyclo[3.2.1]oct-2-ene-2-carboxylate (14:(1RS)-AECG-FP)

The (1RS)-AECG-CN-FP (4.91 mmol) synthesized in Example 10 was dissolved in 2.3 ml of 95% methanol, followed by adding thereto 1.2 ml of concentrated sulfuric acid, and the resulting mixture was stirred with heating at 110° C. for 6 hours. The methanol was evaporated and the residue was neutralized with saturated sodium hydrogencarbonate solution, followed by extraction with ethyl acetate. The organic layer was dried and then distilled to remove the solvent, whereby (1RS)-AECG-FP was obtained.

Example 12

Synthesis of methyl [1RS-(2-exo,3-exo)]-8-(3-fluoropropyl)-3-phenyl-8-azabicyclo[3.2.1]octane-2-carboxylate (15:(1RS)-β-CPT-FP)

In a two-necked flask, 50 ml of anhydrous ether was placed under argon gas and cooled to −40° C. Then, 1.8 ml of 3M ethereal solution of phenylmagnesium bromide was added thereto and the resulting mixture was stirred at −40° C. for 30 minutes. A solution in 50 ml of anhydrous ether of the (1RS)-AECG-FP (2.72 mmol) synthesized in Example 11 was added dropwise thereto, followed by stirring at −40° C. for 4 hours. Thereafter, 20 ml of 1M ethereal solution of hydrochloric acid was added thereto and stirred for 5 minutes. The resulting mixture was cooled to room temperature by adding ice water, and then extracted with ether. The aqueous layer was adjusted to pH 8 with concentrated aqueous ammonia and extracted with ether and chloroform. The resulting organic layer was dried and then distilled to remove the solvent. The crude product thus obtained was purified by silica gel column chromatography (flash chromatography, eluent: hexane/ethyl acetate=20/1 to 1/1) to obtain (1RS)-β-CPT-FP.

Example 13

Synthesis of methyl [1RS-(2-exo,3-exo)]-8-(3-fluoropropyl)-3-(4-iodophenyl)-8-azabicyclo[3.2.1]-octane-2-carboxylate (12:(1RS)-β-CIT-FP)

The (1RS)-β-CPT-FP (1.31 mmol) synthesized in Example 12 and 0.33 g (1.31 mmol) of iodine were dissolved in 4 ml of acetic acid. Then, 0.8 ml of concentrated sulfuric acid and 0.8 ml of concentrated nitric acid were added dropwise thereto and the resulting mixture was stirred with heating at 55° C. for 2 hours in a sealed vessel. After completion of the reaction, the reaction mixture was cooled to room temperature by adding ice water, and adjusted to pH 8 with concentrated aqueous ammonia. This reaction solution was extracted with chloroform, and the organic layer was washed with 10% sodium disulfite solution or sodium thiosulfate solution. The washed organic layer was dried and then distilled to remove the solvent, whereby 0.286 g of a crude product was obtained. The crude product was purified by silica gel column chromatography (eluent: chloroform/methanol=20/1) to obtain (1RS)-β-CIT-FP. Then, the obtained (1RS)-β-CIT-FP was subjected to optical resolution under the same conditions as in Example 8 to obtain optically active (1R)-β-CIT-FP.

Example 14

Synthesis of [1RS-(2-exo,3-exo)]-8-(3-fluoropropyl)-3-phenyl-8-azabicyclo[3.2.1]octane-2-carbonitrile (17:(1RS)-β-CPT-CN-FP)

In a two-necked flask, 50 ml of anhydrous ether was placed under argon gas and cooled to −40° C. Then, 1.8 ml of 3M ethereal solution of phenylmagnesium bromide was added thereto and the resulting mixture was stirred at −40° C. for 30 minutes. Thereafter, a solution in 50 ml of anhydrous ether of the (1RS)-AECG-CN-FP (2.72 mmol) synthesized in Example 10 was added drop-wise thereto while maintaining the temperature at −40° C., and stirred for 4 hours. After 4 hours, 20 ml of 1M ethereal solution of hydrochloric acid was added thereto and stirred for 5 minutes. The resulting mixture was cooled to room temperature by adding ice water, followed by extraction with ether (separation into an organic layer 1 and an aqueous layer 1). The aqueous layer was adjusted to pH 8 with concentrated aqueous ammonia, followed by extraction with ether and chloroform (separation into an organic layer 2 and an aqueous layer 2). The organic layer 2 was dried and then distilled to remove the solvent. The crude product thus obtained was purified by silica gel column chromatography (flash chromatography, eluent: hexane/ethyl acetate=20/1 to 1/1) to obtain (1RS)-β-CPT-CN-FP.

Example 15

Synthesis of methyl [1RS-(2-exo,3-exo)]-8-(3-fluoropropyl)-3-(4-iodophenyl)-8-azabicyclo[3.2.1]-octane-2-carboxylate (12:(1RS)-β-CIT-FP)

The (1RS)-β-CPT-CN-FP (5 mmol) obtained in Example 14 was dissolved in 2.3 ml of 95% methanol, followed by adding thereto 1.2 ml of concentrated sulfuric acid, and the resulting mixture was stirred with heating at 110° C. for 6 hours. The methanol was evaporated and the residue was neutralized with saturated sodium hydrogencarbonate solution, followed by extraction with ethyl acetate. The organic layer was dried and then distilled to remove the solvent, to obtain methyl [1RS-(2-exo,3-exo)]-8-(3-fluoropropyl)-3-phenyl-8-azabicyclo[3.2.1]octane-2-carboxylate (15:(1RS)-β-CPT-FP). This (1RS)-β-CPT-FP (1.31 mmol) and 0.33 g (1.31 mmol) of iodine were dissolved in 4 ml of acetic acid, followed by adding dropwise thereto 0.8 ml of concentrated sulfuric acid and 0.8 ml of concentrated nitric acid, and the resulting mixture was stirred with heating at 55° C. for 2 hours in a sealed vessel. After completion of the reaction, the reaction solution was cooled to room temperature by adding ice water, and adjusted to pH 8 with concentrated aqueous ammonia. This reaction solution was extracted with chloroform, and the organic layer was washed with 10% sodium disulfite solution or sodium thiosulfate solution. The washed organic layer was dried and then distilled to remove the solvent, whereby 0.286 g of a crude product was obtained. The crude product was purified by silica gel column chromatography (eluent: chloroform/methanol=20/1) to obtain (1RS)-β-CIT-FP. The obtained (1RS)-β-CIT-FP was subjected to optical resolution under the same conditions as in Example 8 to obtain optically active (1R)-β-CIT-FP.

Example 16

Synthesis of methyl [1RS-(2-exo,3-exo)]-3-(4-chlorophenyl)-8-methyl-8-azabicyclo[3.2.1]octane-2-carboxylate (20:(1RS)-β-CCIT)

In a two-necked flask, 20 ml of anhydrous ether was placed under argon gas and cooled to −40° C. Then, 3.1 ml of 1M ethereal solution of 4-chlorophenyl-magnesium bromide was added thereto and the resulting mixture was stirred at −40° C. for 30 minutes. A solution in 20 ml of anhydrous ether of 0.475 g (2.62 mmol) of the (1RS)-AECG synthesized in Example 2 was added dropwise thereto, followed by stirring at −40° C. for 4 hours. Thereafter, 15 ml of 1M ethereal solution of hydrochloric acid was added thereto, and the resulting mixture was cooled to room temperature by adding ice water with stirring, and then extracted with ether. The aqueous layer obtained by the ethereal extraction was adjusted to pH 8 with concentrated aqueous ammonia and extracted with chloroform. The chloroform layer was dried and then distilled to remove the solvent, whereby 0.653 g of a light-brown oil was obtained. The light-brown oil was purified by silica gel column chromatography (flash chromatography, eluent: ether/triethylamine=20/1) to obtain 0.241 g of (1RS)-β-CCIT as a light-brown oil (yield: 33%). In the reaction described above, methyl [1RS-(2-endo,3-exo)]-3-(4-chlorophenyl)-8-methyl-8-azabicyclo[3.2.1]octane-2-carboxylate ((1RS)-α-CCIT), i.e., a stereoisomer of (1RS)-β-CCIT was produced as a by-product in addition to (1RS)-β-CCIT. This by-product was recovered, and the compounds thus obtained were identified by proton NMR measurement. The values obtained for each compound by the proton NMR measurement were assigned with reference to the values described in literature (Meltzer et al., J. Med. Chem., 36, 855–862(1993)).

The assignment of the values obtained for each compound by the proton NMR measurement were as follows.
$^1$H-NMR Measurement Results for (1RS)-β-CCIT:
$^1$H-NMR(CDCl$_3$)ppm: 1.6–1.9(m, 3H), 2.0–2.3(m, 2H), 2.22(s, 3H, NCH$_3$), 2.56(dt, 1H), 2.8–3.0(m, 2H), 3.36(m, 1H), 3.50(s, 3H, COOCH$_3$), 3.56(m, 1H), 7.18–7.28(m, 4H, Ar—H).

¹H-NMR Measurement Results for (1RS)-α-CCIT:
 ¹H-NMR(CDCl$_3$)ppm: 1.6–2.3(m, 6H), 2.42(s, 3H, NCH$_3$), 3.0–3.2(m, 2H), 3.26(m, 1H), 3.42(m, 1H), 3.54(s, 3H, COOCH$_3$), 7.18–7.28(m, 4H, Ar—H).

Example 17

Synthesis of [1RS-(2-exo,3-exo)]-3-(4-chlorophenyl)-8-methyl-8-azabicyclo[3.2.1]octane-2-carbonyl Chloride 21

In a mixture of 15 ml of water and 20 ml of 1,4-dioxane was dissolved 1 mmol of the (1RS)-β-CCIT obtained in Example 16, followed by adding thereto 1 ml of 1N hydrochloric acid solution, and the resulting mixture was heated under reflux for several days. After completion of the reaction, the reaction mixture was concentrated, neutralized with sodium carbonate solution, and then extracted with chloroform. The chloroform layer was dried and then distilled to remove the solvent, and the residue was purified by silica gel column chromatography (eluent: chloroform/methanol=5/1 to 3/1) to obtain [1RS-(2-exo,3-exo)]-3-(4-chlorophenyl)-8-methyl-8-azabicyclo[3.2.1]octane-2-carboxylic acid. In 10 ml of dichloromethane was dissolved 1 mmol of the obtained [1RS-(2-exo,3-exo)]-3-(4-chlorophenyl)-8-methyl-8-azabicyclo[3.2.1]octane-2-carboxylic acid. Then, 1 ml of 2M solution of oxalyl chloride in dichloromethane was added thereto under nitrogen at room temperature. The resulting solution was stirred for 1.5 hours and then concentrated at 30° C. to obtain an adhesive oil. The oil was dried under reduced pressure to obtain [1RS-(2-exo,3-exo)]-3-(4-chlorophenyl)-8-methyl-8-azabicyclo[3.2.1]octane-2-carbonyl chloride 21.

Example 18

Synthesis of [1RS-(2-exo,3-exo)]-3-(4-chlorophenyl)-N-[2-[S-(4-methoxybenzyl)thio]ethyl]-8-methyl-8-azabicyclo[3.2.1]octane-2-carboxamide The [1RS-(2-exo,3-exo)]-3-(4-chlorophenyl)-8-methyl-8-azabicyclo[3.2.1]octane-2-carbonyl chloride 21 obtained in Example 17 was dissolved in 10 ml of dichloromethane, and the solution was cooled to −10° C. A solution of 197 mg (1 mmol) of 4-methoxybenzylthioethylamine in 10 ml of dichloromethane and then 0.28 ml (2 mmol) of triethylamine were added thereto under nitrogen, and the resulting mixture was stirred at room temperature for 6 hours. Thereafter, 20 ml of water was added thereto and the desired compound was extracted three times with dichloromethane. The combined organic layer was dried over sodium sulfate and then distilled to remove the solvent. The oil thus obtained was purified by silica gel column chromatography (eluent: ethyl acetate/methanol/aqueous ammonia=8.5/1/0.5) to obtain [1RS-(2-exo,3-exo)]-3-(4-chlorophenyl)-N-[2-[S-(4-methoxybenzyl)thio]ethyl]-8-methyl-8-azabicyclo[3.2.1]-octane-2-carboxamide as an oil.

Example 19

Synthesis of [1RS-(2-exo,3-exo)]-3-(4-chlorophenyl)-2-[[N-[2-[S-(4-methoxybenzyl)thio]ethyl]-amino]methyl]-8-methyl-8-azabicyclo[3.2.1]octane To a solution in 10 ml of tetrahydrofuran of 1 mmol of the [1RS-(2-exo,3-exo)]-3-(4-chlorophenyl)-N-[2-[S-(4-methoxybenzyl)thio]ethyl]-8-methyl-8-azabicyclo[3.2.1]-octane-2-carboxamide obtained in Example 18 was added 5 ml of 1M solution of borane in tetrahydrofuran under nitrogen, and the resulting mixture was heated under reflux for 12 hours. After completion of the reaction, the reaction mixture was cooled and 1N hydrochloric acid solution was added thereto until no more gas evolution was observed. The solution thus obtained was concentrated under reduced pressure. To the resulting adhesive oil was added 10 ml of 1N hydrochloric acid solution, followed by stirring at 90° C. for 30 minutes. The resulting solution was cooled to 0° C., made basic with concentrated aqueous ammonia, and then extracted with dichloromethane. The organic layer was dried and then distilled to remove the solvent, and the crude product thus obtained was purified by silica gel column chromatography (eluent: ethyl acetate/methanol/aqueous ammonia=8.5/1/0.5) to obtain [1RS-(2-exo,3-exo)]-3-(4-chlorophenyl)-2-[[N-[2-[S-(4-methoxybenzyl)thio]ethyl]amino]methyl]-8-methyl-8-azabicyclo[3.2.1]octane.

Example 20

Synthesis of [1RS-(2-exo,3-exo)]-2-[[[3-(4-chlorophenyl)-8-methyl-8-azabicyclo[3.2.1]oct-2-yl]methyl][2-[S-(4-methoxybenzyl)thio]ethyl]amino]-N-[2-[S-(4-methoxybenzyl)thio]ethyl]acetamide In 15 ml of dichloromethane was dissolved 2.46 g (12.5 mmol) of 4-methoxybenzylthioethylamine, and the solution was cooled to −78° C. To this solution were added dropwise a solution of 1 ml (12.5 mmol) of chloroacetyl chloride in 15 ml of dichloromethane and then 1.7 ml (12.5 mmol) of triethylamine. The reaction mixture was allowed to warm to room temperature and then stirred for 1 hour. After extraction by addition of 20 ml of water, the organic layer was washed successively with 1N hydrochloric acid solution, saturated aqueous sodium chloride solution and water. The organic layer was dried and then distilled to remove solvent, to obtain an oil. The oil was dissolved in a mixed solvent of ethyl acetate and hexane and the resulting solution was cooled, after which the solid precipitated was collected by filtration. In 10 ml of acetonitrile were dissolved 0.548 g (2 mmol) of the collected solid and the [1RS-(exo,exo)]-3-(4-chlorophenyl)-2-[[N-[2-[S-(4-methoxybenzyl)thio]ethyl]-amino]methyl]-8-methyl-8-azabicyclo[3.2.1]octane obtained in Example 19, followed by adding thereto 0.28 ml (2 mmol) of triethylamine, and the resulting mixture was heated under reflux for 12 hours. After completion of the reaction, the reaction mixture was concentrated and then extracted with dichloromethane. The organic layer was dried and then distilled to remove the solvent, and the crude product thus obtained was purified by silica gel column chromatography (eluent: chloroform/methanol=9/1 to 8/2) to obtain [1RS-(2-exo,3-exo)]-2-[[[3-(4-chlorophenyl)-8-methyl-8-azabicyclo[3.2.1]oct-2-yl]methyl][2-[S-(4-methoxybenzyl)thio]ethyl]amino]-N-[2-[S-(4-methoxybenzyl)-thio]ethyl]acetamide as an oil.

Example 21

Synthesis of [1RS-(2-exo,3-exo)]-2-[[2-[[[3-(4-chlorophenyl)-8-methyl-8-azabicyclo[3.2.1]oct-2-yl]methyl]][S-(4-methoxybenzyl)thio]ethyl]amino]ethyl]-amino]-S-(4-methoxybenzyl)ethanethiol 22

To a solution in 10 ml of tetrahydrofuran of 1 mmol of the [1RS-(2-exo,3-exo)]-2-[[[3-(4-chlorophenyl)-8-methyl-8-azabicyclo[3.2.1]oct-2-yl]methyl][2-[S-(4-methoxybenzyl)thio]ethyl]amino]-N-[2-[S-(4-methoxybenzyl)thio]ethyl]acetamide obtained in Example 20 was added 1.5 ml of 1M solution of borane in tetrahydrofuran under nitrogen. The resulting solution was refluxed for 12 hours. After completion of the reaction, the reaction solution was cooled, and 1N hydrochloric acid solution was added thereto until no more gas evolution was observed. The solution thus obtained was concentrated under reduced pressure. To the concentrate was added 10 ml of 1N hydrochloric acid solution, followed by stirring at 90° C. for 30 minutes. The resulting solution was cooled to 0° C., made basic with concentrated aqueous ammonia, and then extracted with dichloromethane. The organic layer was dried and then distilled to remove the solvent, and the crude product thus obtained was purified by silica gel column chromatography (eluent: ethyl acetate/methanol/aqueous ammonia=8.5/1/0.5) to obtain the desired compound [1RS-(2-exo,3-exo)]-2-[[2-[[[3-(4-chlorophenyl)-8-methyl-8-azabicyclo[3.2.1]oct-2-yl] methyl][[S-(4-methoxybenzyl)thio]ethyl]amino]ethyl] amino]-S-(4-methoxybenzyl)ethanethiol 22.

Example 22

Synthesis of [1RS-(2-exo,3-exo)]-2-[[2-[[[3-(4-chlorophenyl)-8-methyl-8-azabicyclo[3.2.1]oct-2-yl] methyl](2-sulfanilethyl)amino]ethyl]amino]-ethanethiol trifluoroacetate 23

In a mixture of 7.5 ml of trifluoroacetic acid (TFA) and 0.25 ml of anisole was dissolved at 0° C. 1 mmol of the [1RS-(2-exo,3-exo)]-2-[[2-[[[3-(4-chlorophenyl)-8-methyl-8-azabicyclo[3.2.1]oct-2-yl]methyl][[S-(4-methoxybenzyl) thio]ethyl]amino]-ethyl]amino]-S-(4-methoxybenzyl) ethanethiol 22 obtained in Example 21, and 0.636 g (2 mmol) of mercury acetate (Hg(OAc)$_2$) was added thereto. The resulting mixture was stirred at room temperature for 30 minutes. After completion of the reaction, the solvent was evaporated under reduced pressure. To the oil thus obtained was added 10 ml of anhydrous ether to effect dissolution and the resulting suspension was subjected to dissolution by applying super sonic waves. The solid formed from the solution was collected by filtration by suction. The collected solid was dried under reduced pressure and dissolved in 10 ml of ethanol. Through the resulting solution, hydrogen sulfide gas was bubbled for 20 minutes, followed by filtration through Celite. The filtrate was concentrated to obtain [1RS-(2-exo,3-exo)]-2-[[2-[[[3-(4-chlorophenyl)-8-methyl-8-azabicyclo[3.2.1]oct-2-yl]methyl](2-sulfanilethyl)-amino]ethyl]amino]ethanethiol trifluoroacetate 23.

Optically active [1R-(2-exo,3-exo)]-2-[[2-[[[3-(4-chlorophenyl)-8-methyl-8-azabicyclo[3.2.1]oct-2-yl] methyl](2-sulfanilethyl)amino]ethyl]amino]-ethanethiol trifluoroacetate can be obtained by carrying out optical resolution under the same conditions as in Example 8, in a proper stage of the synthesis of this optically active compound in view of the yields of intermediates for the synthesis, and the like.

Example 23

Synthesis of [1RS-(2-exo,3-exo)]-3-(4-chlorophenyl)-8-methyl-8-azabicyclo[3.2.1]octane-2-carbonitrile (25:(1RS)-β-CCIT-CN)

In a two-necked flask, 20 ml of anhydrous ether was placed under argon gas and cooled to −40° C. Then, 3 ml of 1M ethereal solution of 4-chlorophenyl-magnesium bromide was added thereto and the resulting mixture was stirred at −40° C. for 30 minutes. A solution in 20 ml of anhydrous ether of 2.18 mmol of the (1RS)-AECG-CN synthesized in Example 1 was added dropwise thereto, followed by stirring at −40° C. for 4 hours. Thereafter, 6 ml of 1M ethereal solution of hydrochloric acid was added thereto, and the resulting mixture was cooled to room temperature by adding ice water with stirring, and then extracted with ether. The aqueous layer was adjusted to pH 8 with concentrated aqueous ammonia and extracted with ether (re-extraction with ether was carried out by adding aqueous ammonia). The organic layer obtained by the extraction of the basic solution was dried and then distilled to remove the solvent. The residue was purified by silica gel column chromatography (flash chromatography, eluent: chloroform/triethylamine=50/1) to obtain (1RS)-β-CCIT-CN.

Example 24

Synthesis of [1RS-(2-exo,3-exo)]-2-[[2-[[[3-(4-chlorophenyl)-8-methyl-8-azabicyclo[3.2.1]oct-2-yl] methyl](2-sulfanilethyl)amino]ethyl]amino]-ethanethiol trifluoroacetate 23 (the reaction scheme G)

Tetrahydrofuran dehydrated solvent was placed in a flask in which the air had been replaced with argon gas, and 114 mg of lithium aluminum hydride (LAH) was added thereto. To the resulting solution was added dropwise a solution in 3 ml of tetrahydrofuran of 1 mmol of the (1RS)-β-CCIT-CN obtained in Example 23, and the solution thus obtained was refluxed. After completion of the reaction, the reaction solution was cooled to room temperature, followed by adding dropwise thereto water under ice-cooling. Then, sodium hydroxide was added thereto. The amine released was extracted three times with ether and the combined organic layer was dried over sodium carbonate and then distilled to remove the solvent, to obtain [1RS-(2-exo,3-exo)]-2-aminomethyl-3-(4-chlorophenyl)-8-methyl-8-azabicyclo[3.2.1]octane 26. In dichloromethane was dissolved 1 mmol of the obtained [1RS-(2-exo,3-exo)]-2-aminomethyl-3-(4-chlorophenyl)-8-methyl-8-azabicyclo-[3.2.1]octane. To the resulting solution were added 1.1 mmol of 4-methoxybenzylmercaptoacetic acid and 1.1 mmol of triethylamine at 0° C., and the resulting mixture was stirred at room temperature for 24 hours. After completion of the reaction, the solvent was evaporated, followed by extraction with ethyl acetate. The organic layer was dried and then distilled to remove the solvent, to obtain [1RS-(2-exo,3-exo)]-3-(4-chlorophenyl)-N-[2-[[S-(4-methoxybenzyl) thio]-carbamoyl]methyl]-8-methyl-8-azabicyclo[3.2.1] octane. Then, this compound was reduced in the same manner as in Example 19 to obtain [1RS-(2-exo,3-exo)]-3-(4-chlorophenyl)-2-[[N-[2-[S-(4-methoxybenzyl)thio]-ethyl]amino]methyl]-8-methyl-8-azabicyclo[3.2.1]octane. From this [1RS-(2-exo,3-exo)]-3-(4-chlorophenyl)-2-[[N-[2-[S-(4-methoxybenzyl)thio]ethyl]amino]methyl]-8-methyl-8-azabicyclo[3.2.1]octane, [1RS-(2-exo,3-exo)]-2-[[2-[[[3-(4-chlorophenyl)-8-methyl-8-azabicyclo-[3.2.1] oct-2-yl]methyl][[S-(4-methoxybenzyl)thio]-ethyl]amino] ethyl]amino]-S-(4-methoxybenzyl)ethanethiol 22 was obtained in the same manner as in Examples 20 and 21. Subsequently, [1RS-(2-exo,3-exo)]-2-[[2-[[[3-(4-chlorophenyl)-8-methyl-8-azabicyclo[3.2.1]oct-2-yl] methyl](2-sulfanilethyl)amino]ethyl]-amino]ethanethiol trifluoroacetate 23 was obtained in the same manner as in Example 22. optically active [1R-(2-exo,3-exo)]-2-[[2-[[[3-(4-chlorophenyl)-8-methyl-8-azabicyclo[3.2.1]oct-2-yl] methyl](2-sulfanilethyl)amino]ethyl]amino]ethanethiol trifluoroacetate can be obtained by carrying out optical resolution under the same conditions as in Example 8, in a proper stage of the synthesis of this optically active compound in view of the yields of intermediates for the synthesis, and the like.

What is claimed is:

1. A process for synthesizing a phenyltropane compound represented by the formula (4):

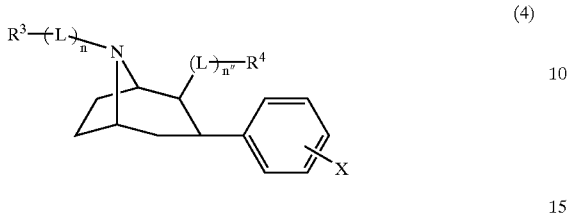

(4)

wherein $R^3$ is a group selected from the group consisting of an unsubstituted alkyl group, a substituted alkyl group, an unsubstituted aralkyl group, a substituted aralkyl group and a chelating group capable of forming a complex together with a radioactive transition metal; $R^4$ is a group selected from the group consisting of an alkyl ester group and a chelating group capable of forming a complex together with a radioactive transition metal; L is a methylene chain of 1 to 4 carbon atoms as a connecting portion; n' and n'' are independently an integer of 1 or 0; and X is a hydrogen atom, an alkyl group, an alkoxy group, or a halogen atom or its radioisotope, which comprises reacting an anhydroecognine intermediate compound of the following formula (3) with substituted or unsubstituted phenylmagnesium bromide, wherein the compound of formula (3) is obtained by a process which comprises reacting a cycloheptatriene compound represented by the formula (1):

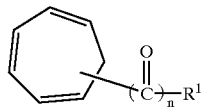

(1)

wherein n is an integer of 0 or 1; and $R^1$ is a cyano group in the case of n being 0, and $R^1$ is selected from an alkyl group and a $C_{7-10}$ aralkyl group in the case of n being 1, with a primary amine represented by the formula (2):

$$R^2NH_2 \qquad (2)$$

wherein $R^2$ is a hydrogen atom, an unsubstituted alkyl group, a substituted alkyl group, an unsubstituted $C_{7-10}$ aralkyl group or a substituted $C_{7-10}$ aralkyl group, or a salt thereof or ammonia in the presence of a base to obtain an anhydroecgonine compound represented by the formula (3):

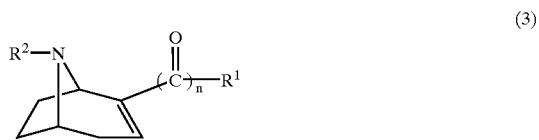

(3)

wherein $R^1$ and $R^2$ as defined above.

2. A process for synthesizing a phenyltropane compound according to claim 1, wherein the chelating group capable of forming a complex together with a radioactive transition metal is a group selected from the group consisting of a diaminodithiol, a monoamidomonoaminodithiol, a diamidothiol and a triamidothiol.

3. A process for synthesizing a phenyltropane compound according to claim 2, wherein the diaminodithiol is N,N'-bis(2-mercaptoethyl)ethylenediamine or 2,2,9,9-tetramethyl-4,7-diaza-1,10-decanethiol; the monoamidomonoaminodithiol is N-2-mercaptoethyl-2-mercaptoethylaminoacetamide or N-(2-mercaptoethyl)-aminoethyl-2-mercaptoacetamide; the diamidodithiol is 1,2-ethylenebis(2-mercaptoacetamide); and the triamidothiol is mercaptoacetylglycylglycylglycine.

* * * * *